United States Patent
Huang

(10) Patent No.: US 10,368,797 B2
(45) Date of Patent: Aug. 6, 2019

(54) SYSTEM FOR MONITORING SLEEP EFFICIENCY

(71) Applicant: Tsung-Cheng Huang, Taichung (TW)

(72) Inventor: Tsung-Cheng Huang, Taichung (TW)

( * ) Notice: Subject to any disclaimer, the term of this patent is extended or adjusted under 35 U.S.C. 154(b) by 0 days.

(21) Appl. No.: 15/972,299

(22) Filed: May 7, 2018

(65) Prior Publication Data
US 2018/0325450 A1     Nov. 15, 2018

(30) Foreign Application Priority Data

May 12, 2017  (TW) .............................. 106115731 A

(51) Int. Cl.
  *A61B 5/00*       (2006.01)
  *A61B 5/01*       (2006.01)
  *A61B 5/0476*    (2006.01)

(52) U.S. Cl.
  CPC .............. *A61B 5/4812* (2013.01); *A61B 5/01* (2013.01); *A61B 5/4815* (2013.01); *A61B 5/0476* (2013.01); *A61B 5/4809* (2013.01)

(58) Field of Classification Search
  CPC combination set(s) only.
  See application file for complete search history.

(56) References Cited

U.S. PATENT DOCUMENTS

| | | | |
|---|---|---|---|
| 9,492,086 B2 * | 11/2016 | Ewers ............... | A61M 16/0666 |
| 9,750,415 B2 * | 9/2017 | Breslow ............. | A61B 5/02405 |
| 9,962,123 B2 * | 5/2018 | Benson .................. | G16H 50/30 |
| 9,968,293 B1 * | 5/2018 | Kahn .................... | A61B 5/4812 |
| 10,004,406 B2 * | 6/2018 | Yuen ..................... | A61B 5/0205 |
| 2016/0136385 A1 * | 5/2016 | Scorcioni ............. | A61M 21/02 600/26 |
| 2017/0100076 A1 * | 4/2017 | Benson ................... | G16H 50/30 |

FOREIGN PATENT DOCUMENTS

CN   105942777 A   9/2016

OTHER PUBLICATIONS

P. J. Murphy and S. S. Campbell, "Nighttime drop in body temperature: a physiological trigger for sleep onset?" Sleep, 20(7), pp. 505-511, 1997.
Search Report appended to an Office Action, which was issued to Taiwanese counterpart application No. 106115731 by the TIPO dated Feb. 22, 2018, with an English translation thereof.
Search Report appended to an Office Action, which was issued to Taiwanese counterpart application No. 106115731 by the TIPO dated Apr. 25, 2018, with an English translation thereof.

* cited by examiner

*Primary Examiner* — Travis R Hunnings
(74) *Attorney, Agent, or Firm* — Trop, Pruner & Hu, P.C.

(57) ABSTRACT

A system for monitoring sleep efficiency includes a measuring device and a data processing device. The measuring device is for measuring body temperature of a subject and for outputting temperature data associated with the body temperature. The data processing device receives the temperature data, and is programmed to process the temperature data so as to determine sleep efficiency. The processing of the temperature data includes constructing a curve of the body temperature over asleep episode, finding a saddle point of the curve occurring for a first time, treating a time instance at which the saddle point occurs as a sleep-onset time point at which the subject falls asleep, and determining the sleep efficiency according to the sleep-onset time point.

6 Claims, 6 Drawing Sheets

_US 10,368,797 B2_

SYSTEM FOR MONITORING SLEEP EFFICIENCY

CROSS-REFERENCE TO RELATED APPLICATION

This application claims priority of Taiwanese Patent Application No. 106115731, filed on May 12, 2017.

FIELD

The disclosure relates to a system for monitoring sleep, particularly to a system that is capable of performing continuous monitoring of sleep efficiency.

BACKGROUND

Conventionally, monitoring sleep of a person is implemented by an electroencephalography (EEG) device. The EEG device is capable of recording, during a sleep episode of the person, EEG data of the person and identifying a non-rapid eye movement (NREM) period and a rapid eye movement (REM) period. Other characteristics regarding the sleep episode may be obtained by analyzing the EEG data.

Taiwanese Patent No. 1405559 discloses a handheld sleep assistant device that enables a user to record biophysiological information and provides assistance regarding sleep for the user.

SUMMARY

Therefore, an object of the disclosure is to provide a system for monitoring sleep efficiency.

According to one embodiment of the disclosure, the system includes a measuring device and a data processing device.

The measuring device is for measuring body temperature of a subject and for outputting temperature data associated with the body temperature.

The data processing device is coupled with the measuring device for receiving the temperature data therefrom, and is programmed to process the temperature data so as to determine sleep efficiency;

The processing of the temperature data includes constructing a curve of the body temperature over a sleep episode, finding a saddle point of the curve occurring for a first time, treating a time instance at which the saddle point occurs as a sleep-onset time point at which the subject falls asleep, and determining the sleep efficiency according to the sleep-onset time point.

BRIEF DESCRIPTION OF THE DRAWINGS

Other features and advantages of the disclosure will become apparent in the following detailed description of the embodiments with reference to the accompanying drawings, of which.

DETAILED DESCRIPTION

Figure 1:
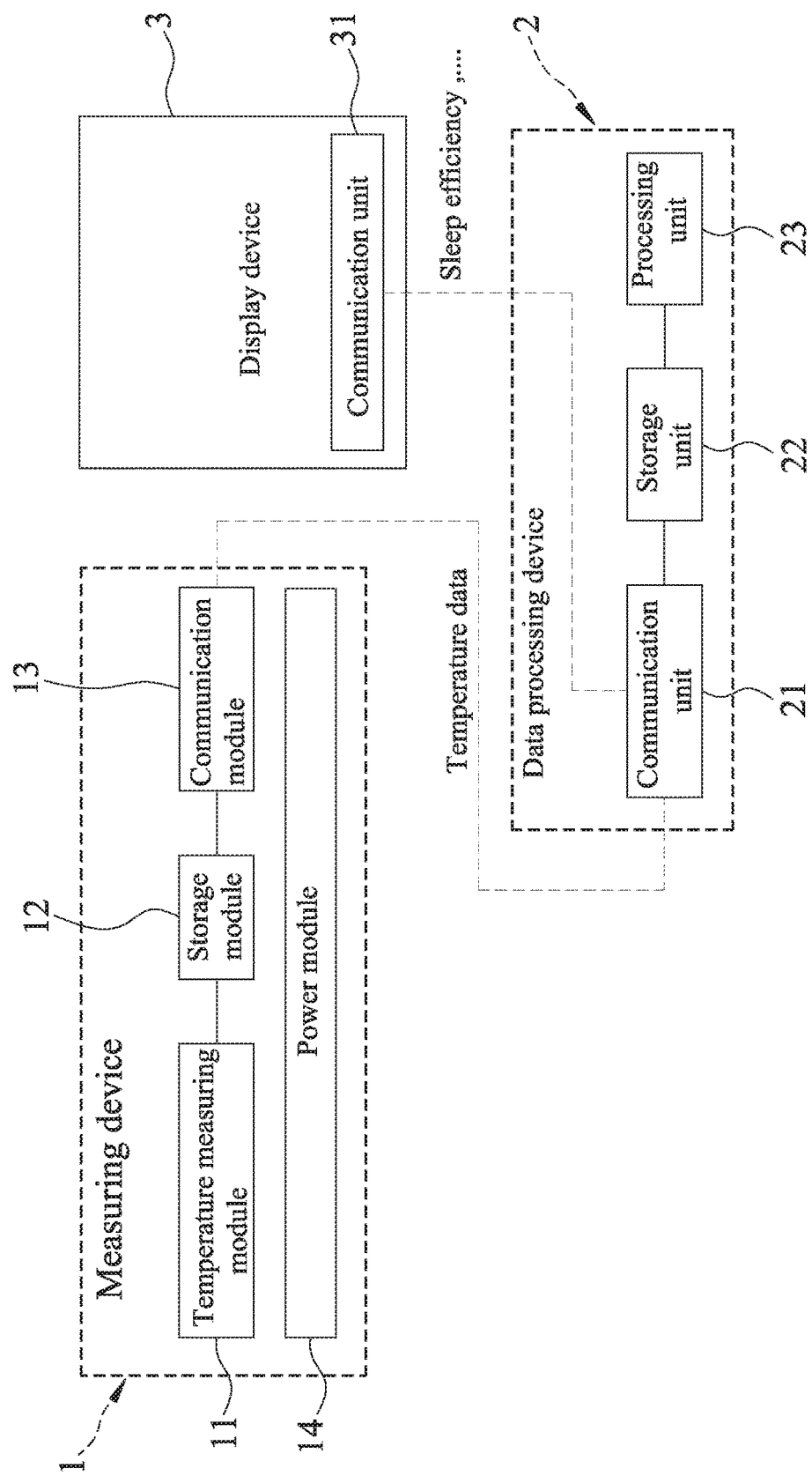
FIG. 1 is a block diagram illustrating a system for monitoring sleep efficiency, according to one embodiment of the disclosure.

Before the disclosure is described in greater detail, it should be noted that where considered appropriate, reference numerals or terminal portions of reference numerals have been repeated among the figures to indicate corresponding or analogous elements, which may optionally have similar characteristics.

FIG. 1 is a block diagram illustrating a system for monitoring sleep efficiency, according to one embodiment of the disclosure. The system includes a measuring device 1, and a data processing device 2 communicating with the measuring device 1. The system may further include a display device 3 communicating with the data processing device 2.

The measuring device 1 is configured to measure body temperature of a subject (e.g., a person) and for outputting temperature data associated with the body temperature. Specifically, the measuring device 1 includes a temperature measuring module 11, a storage module 12, a communication module 13 and a power module 14. The power module 14 is, for example, a battery for providing power for the measuring device 1.

The temperature measuring module 11 measures the body temperature of the subject, and outputs the temperature data to the storage module 12 which may be embodied using, for example, a flash memory device. The communication module 13 is connected to the storage module 12, and is configured for transmitting the temperature data stored in the storage module 12. In use, the communication module 13 may be embodied using a universal serial bus (USB) interface, and/or a wireless communication component that supports wireless data transmissions such as Bluetooth®, Wi-Fi or cellular network.

In this embodiment, the measuring device 1 is integrated in the form of a thermometer patch that can be directly in contact with a part the body of the subject (e.g., armpit). Using the thermometer patch that measures the body temperature through contact, the measurement may be implemented without interference from ambient environment. It is noted that within a 90-second test time, the measuring device 1 has an accuracy within ±0.05 degrees. That is to say, the measuring device 1 is capable of obtaining, within 90 seconds, the body temperature of the subject with an error less than ±0.05 degrees.

The data processing device 2 is coupled with the communication module 13 of the measuring device 1 for receiving the temperature data therefrom, and is programmed to process the temperature data so as to determine sleep efficiency. In this embodiment, the data processing device 2 may be embodied using a portable electronic device (e.g., a smartphone), but may be embodied using a server device that communicates with the measuring device 1 wirelessly in other embodiments.

The data processing device 2 includes a communication unit 21 that supports data transmission with the communication module 13 using wired or wireless transmission, a storage unit 22 that stores the temperature data received from the measuring device 1, and a processing unit 23. The communication unit 21 is, for example, a USB interface or a wireless communication component that supports wireless data transmissions such as Bluetooth®, Wi-Fi or cellular network. The storage unit 22 is, for example, a built-in memory device of the portable electronic device, such as a flash memory, a mobile DDR, etc. The processing unit 23 may be, but not limited to, a single core processor, a multi-core processor, a dual-core mobile processor, a microprocessor, a microcontroller, a digital signal processor (DSP), a field-programmable gate array (FPGA), an application specific integrated circuit (ASIC), etc.

In use, the subject may place the measuring device 1 on his/her skin, and then activate the measuring device 1 before going to sleep. During a sleep episode of the subject, the measuring device 1 continuously measures the body temperature of the subject. When the subject wakes up, the subject may deactivate the measuring device 1 and the measurement is stopped. The temperature data thus generated is then transmitted to the data processing device 2 for analysis. The term "sleep episode" refers to a duration from into-bed time at which the subject goes to bed to a time at which the subject gets out of bed and removes or turns off the measuring device 1.

Figure 2:
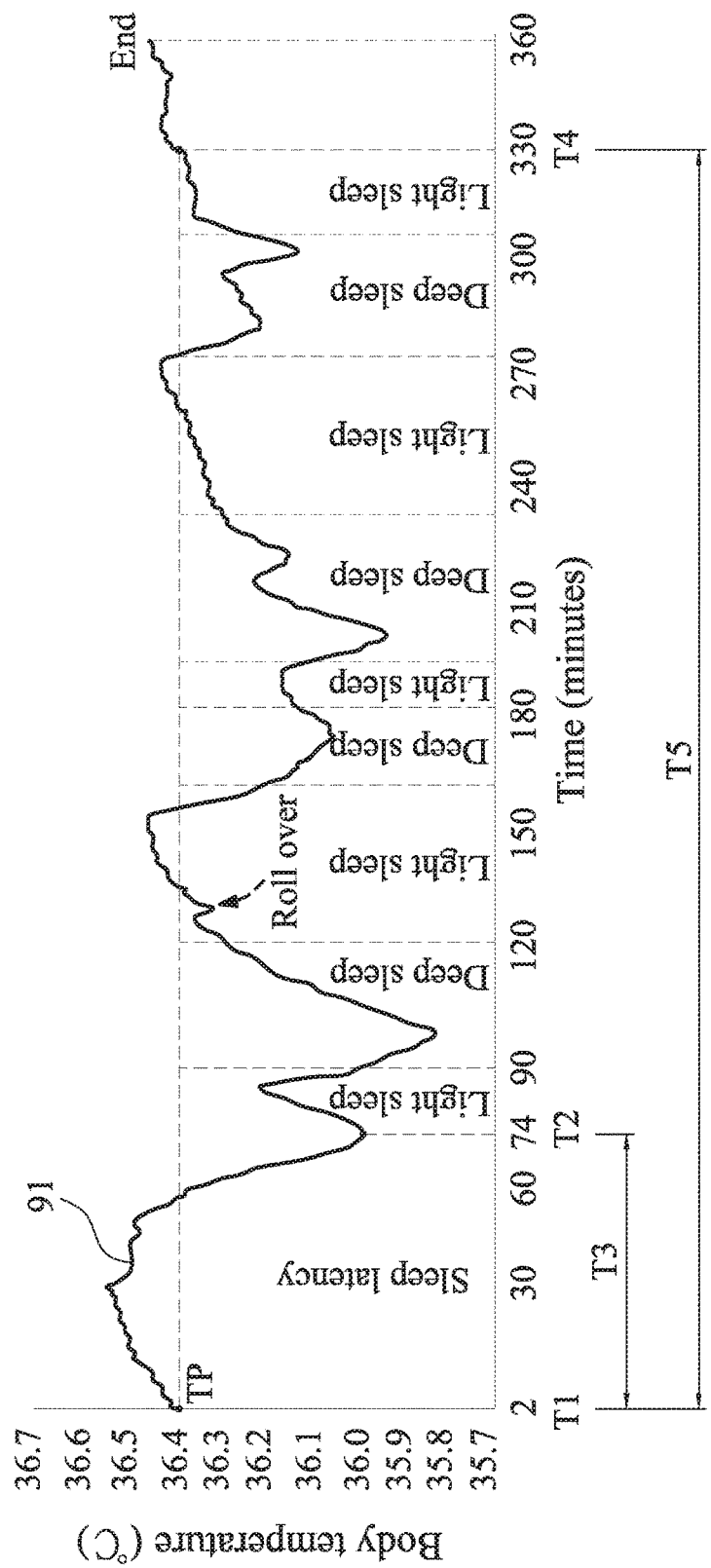
FIG. 2 illustrates a curve of body temperature of a subject obtained by actual experiment on the subject during a sleep episode.

FIG. 2 is a chart illustrating changes of the body temperature of the subject during asleep episode (e.g., a first day). The body temperature of the subject shown in FIG. 2 is obtained by actual experiment on the subject during the sleep episode. In this embodiment, the processing unit 23 processes the temperature data to construct a curve of the body temperature over the sleep episode, and the curve is shown in FIG. 2.

Using the curve of the body temperature, the processing unit 23 is programmed to obtain an into-bed time point (T1) at which the subject goes to bed, a sleep-onset time point (T2) at which the subject falls asleep, and a sleep latency (T3) from the into-bed time point (T1) to the sleep-onset time point (T2).

In this embodiment, the into-bed time point (T1) is defined as a time instance at which the measuring device 1 is activated to measure the body temperature of the subject (e.g., the second minute in FIG. 2). The sleep-onset time point (T2) is obtained by finding a saddle point of the curve occurring for a first time (e.g., the 74$^{th}$ minute in FIG. 2), and treating a time instance at which the saddle point occurs as the sleep-onset time point (T2). In the example as shown in FIG. 2, the sleep latency (T3) equals 74−2=72 minutes.

The processing unit 23 is then programmed to determine a sleep efficiency according to the sleep latency (T3), which is a duration from the into-bed time point (T1) to the sleep-onset time point (T2). In this embodiment, when the sleep latency (T3) is not shorter than a first predetermined threshold (e.g., 30 minutes), the processing unit 23 determines the sleep efficiency as poor. When the sleep latency (T3) is shorter than the first predetermined threshold but not shorter than a second predetermined threshold (e.g., 15 minutes) that is shorter than the first predetermined threshold, the processing unit 23 determines the sleep efficiency as normal. When the sleep latency (T3) is shorter than the second predetermined threshold, the processing unit 23 determines the sleep efficiency as good.

It is noted that in various embodiments, the determination of the sleep efficiency may be done using other standards and may be categorized into other possible results. In some embodiments, the processing unit 23 may determine the sleep efficiency using grading scales from 1 to 10.

Using the curve of the body temperature, the processing unit 23 is further programmed to obtain an initial degree of the body temperature at the into-bed time point (T1), an awakening time point (T4) at which the subject awakens from sleep, and a total sleep time (T5) between the into-bed time point (T1) and the awakening time point (T4).

In this embodiment, the processing unit 23 determines the awakening time point (T4) as a time instance when the body temperature of the subject rises and stays above the initial degree until the end of the sleep episode. In the example shown in FIG. 2, such an instance occurred at the 330$^{th}$ minute. In particular, the subject removes or turns off the measuring device 1 at the 360$^{th}$ minute after waking up, so that the curve shown in FIG. 2 terminates at the 360$^{th}$ minute that is treated as the end of the sleep episode.

In one embodiment, the processing unit 23 obtains a sleep status report indicating a number of changes between light sleep and deep sleep during the sleep episode. The sleep status report may further include a number of times the subject turns his/her body over during the sleep episode.

Based on the sleep status report, the processing unit 23 may obtain asleep quality degree. Specifically, the sleep quality degree may be a ratio of the total number of changes between light sleep and deep sleep during the sleep episode to the total sleep time of the sleep episode. In other embodiments, the sleep quality degree may be a normalized value.

The display device 3 may be embodied using a liquid crystal display (LCD) device or an electronic device with display functionality, and includes a communication unit 31 for receiving the temperature data and the processed data (i.e., the into-bed time, the initial degree, the sleep status report, etc.) from the data processing device 2, and for displaying the data received. It is noted that the data processing device 2 may selectively transmit the processed data to the display device 3 based on actual use. For example, the data processing device 2 may only transmit the sleep efficiency to the display device 3.

It is noted that the sleep efficiency may be displayed in the form of a value, a text or an image (e.g., a face, a symbol, etc.). For example, the display device 3 may display a smiling face to indicate that the sleep efficiency is good, and display a crying face to indicate that the sleep efficiency is poor.

The body temperature of the subject may be utilized in determining many characteristics regarding sleep of the subject based on the following theories.

Firstly, the body temperature of a normal person may change with a periodic pattern based on external factors such as sunrise, sunset, etc., and internal factors within the body of the person such as melatonin produced by the endocrine system (pineal gland) of the person. For example, the body temperature is typically higher during daytime, when human activities are conducted, compared to the body temperature at night, when the person is at rest.

Additionally, in response to changes of the external/internal factors, a change in the body temperature may be less severe compared to other biophysiological signals such as electroencephalography (EEG), heartbeat or blood pressure, since human is homeotherm. Accordingly, it may be beneficial to utilize the body temperature as an indicator for long term sleep monitoring and automatic analysis, as the curve of body temperature typically includes less irregular changes that may require a professional to interpret.

Based on researches started from 1953 A.D., in a sleep episode, the subject alternates between a non-rapid eye movement (NREM) period and a rapid eye movement (REM) period.

From a research in 1982 A.D. (M. Gillberg and T. Akerstedt, "Body temperature and sleep at different times of day," *Sleep*, 5, pp. 378-388, 1982), it is found that the body temperature typically decreases after the into-bed time, and increases after the awakening time.

From a research in 1997 A.D. (P. J. Murphy and S. S. Campbell, "Nighttime drop in body temperature: a physiological trigger for sleep onset?" *Sleep*, 20, pp. 505-511, 1997), it is found that the body temperature decreases the most during a time period before the sleep-onset time.

Based on observations by the applicant, it is found that as the subject enters the REM period, the body temperature increases as his/her breathing becomes faster and irregular.

Figure 3:
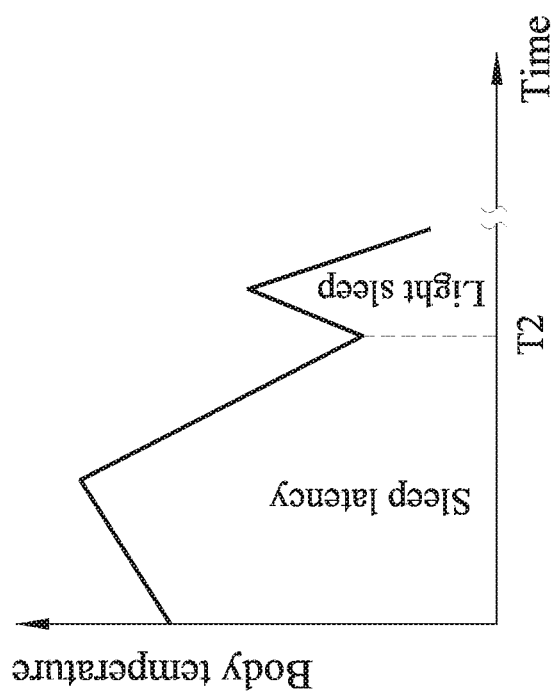
FIG. 3 schematically illustrates a saddle point of a curve of body temperature being treated as a sleep-onset time point.

It may be deduced that in the curve of the body temperature over a sleep episode, a time instance at which a saddle point of the curve occurring for a first time may be treated as the sleep-onset time point (T2) (see FIG. 3 as a schematic example).

In the example shown in FIG. 2, the into-bed time point (T1) is at the $2^{nd}$ minute, the initial degree is 36.38° C. at the into-bed time point (T1), the sleep-onset time point (T2) is at the $74^{th}$ minute, and the sleep latency (T3) is 72 minutes. Using the determination as described above, since the sleep latency (T3) is longer than the first predetermined threshold (i.e., 30 minutes), the processing unit 23 determines the sleep efficiency as poor.

Additionally, the end of the sleep episode (i.e., the time the subject removes the measuring device 1 from the body) is at the $360^{th}$ minute, the awakening time point (T4) is at the $330^{th}$ minute, and the total sleep time (T5) is 328 minutes (i.e., approximately 5.5. hours).

Using the temperature data, the processing unit 23 is programmed to further process the temperature data to obtain the sleep status report indicating a total number of changes between light sleep and deep sleep during the sleep episode. In this example, the total number of changes is 8. In some embodiments, the sleep status report further indicates a number of roll-overs (i.e., the subject turning his/her body over) occurred during the sleep episode. In this example, the number of roll-overs is 1.

Based on the sleep status report, the processing unit 23 is programmed to obtain the sleep quality degree. In this example, the sleep quality degree is 8/328–24.4%.

Figure 4:
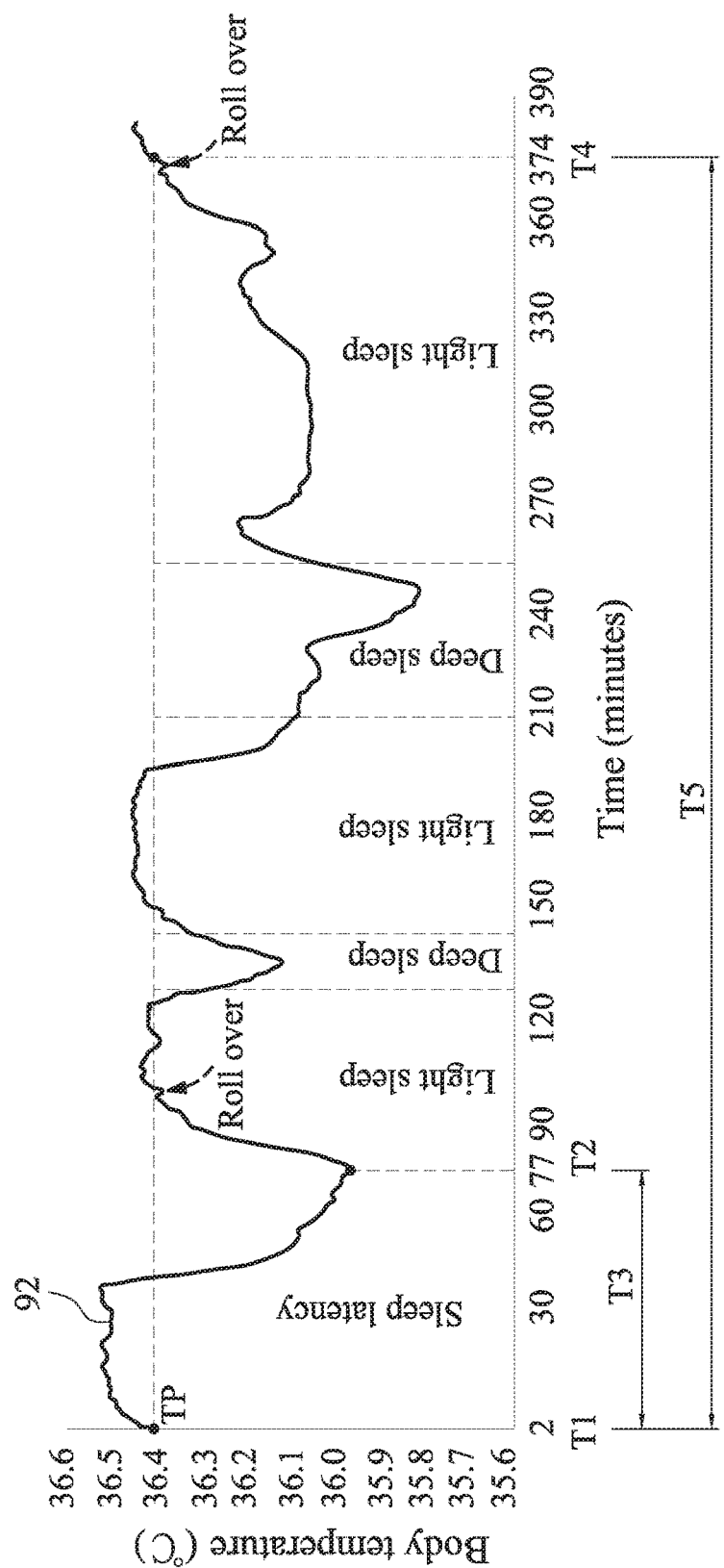
FIGS. 4 and 5 each illustrates a curve of body temperature of a subject obtained by actual experiment on the subject during a sleep episode.

FIG. 4 illustrates a curve of body temperature of the subject obtained by actual experiment on the subject during another sleep episode (e.g., a second day).

In this example, the into-bed time point (T1) is at the $2^{nd}$ minute, the initial degree is 36.38° C., the sleep-onset time point (T2) is at the $77^{th}$ minute, and the sleep latency (T3) is 75 minutes. Using the determination algorithm as described above, since the sleep latency (T3) is longer than the first predetermined threshold (30 minutes), the processing unit 23 determines the sleep efficiency as poor.

Additionally, the end of the sleep episode (i.e., the time the subject removes the measuring device 1) is at the $390^{th}$ minute, the awakening time point (T4) is at $374^{th}$ minute, and the total sleep time (T5) is 372 minutes (i.e., approximately 6.2 hours).

Using the temperature data, the processing unit 23 is programmed to further process the temperature data to obtain the sleep status report indicating the number of changes between light sleep and deep sleep during the sleep episode. In this example, the total number of changes is 4. In some embodiments, the sleep status report further indicates the total number of roll-overs occurred during the sleep episode. In this example, the number of roll-overs is 2.

Based on the sleep status report, the processing unit 23 is programmed to obtain the sleep quality degree. In this example, the sleep quality degree is 4/372=10.8%, which is lower than that in the first day.

Figure 5:
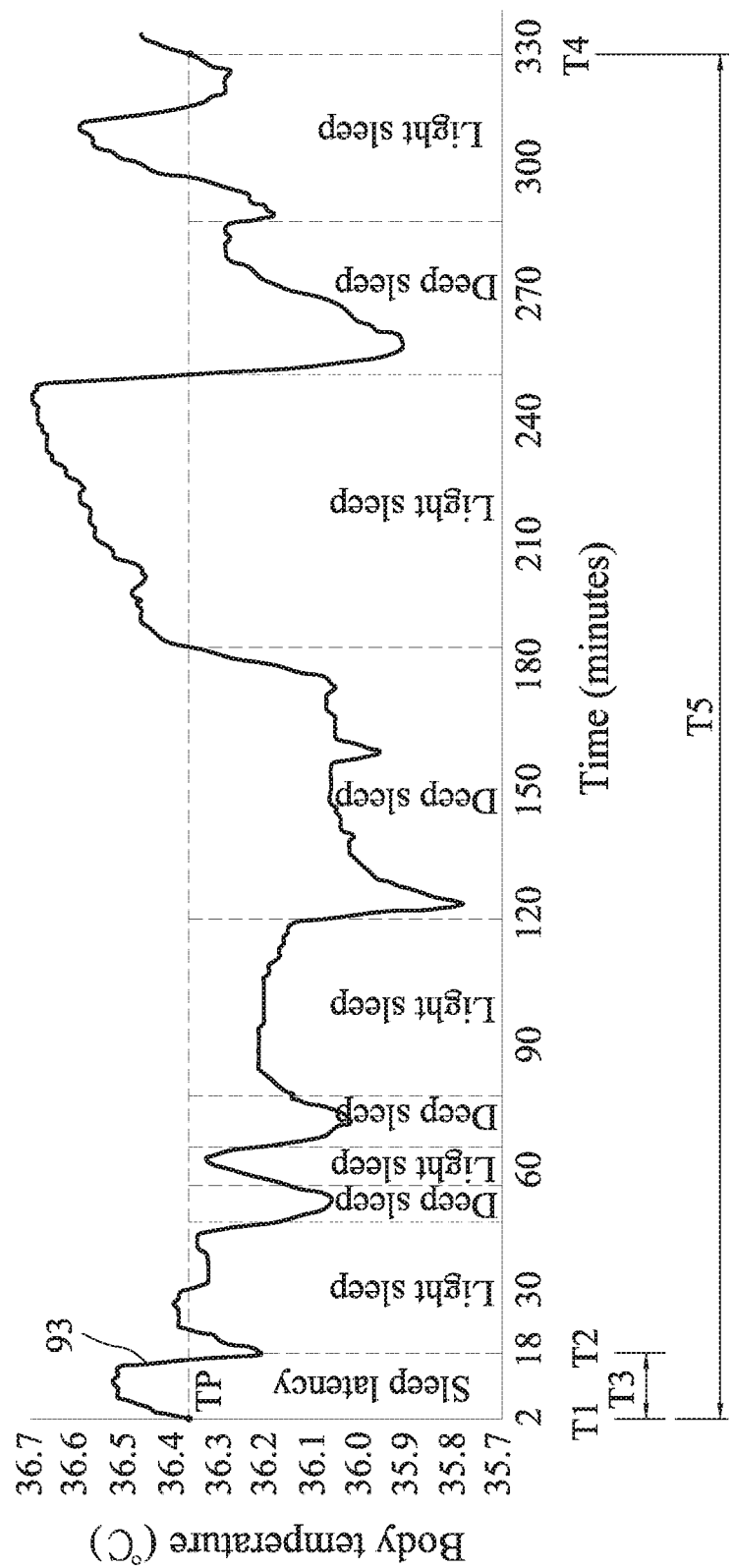

FIG. 5 illustrates a curve of body temperature of the subject obtained by actual experiment on the subject during yet another sleep episode (e.g., a third day).

In this example, the into-bed time point (T1) is at the $2^{nd}$ minute, the initial degree is 36.36° C., the sleep-onset time point (T2) is at the $18^{th}$ minute, and the sleep latency (T3) is 16 minutes. Using the determination algorithm as described above, since the sleep latency (T3) is shorter than the first predetermined threshold (30 minutes) but longer than the second predetermined threshold (15 minutes), the processing unit 23 determines the sleep efficiency as normal.

Additionally, the end of the sleep episode is at the $330^{th}$ minute, the awakening time (T4) is at the $330^{th}$ minute, and the total sleep time (T5) is 328 minutes (i.e., approximately 5.5 hours).

Using the temperature data, the processing unit 23 is programmed to further process the temperature data to obtain the sleep status report indicating the total number of changes between light sleep and deep sleep during the sleep episode. In this example, the total number of changes is 8. In some embodiments, the sleep status report further indicates a number of roll-overs occurred during the sleep episode. In this example, the number of roll-overs is 0.

Based on the sleep status report, the processing unit 23 is programmed to obtain the sleep quality degree. In this example, the sleep quality degree is 8/328=24.4%, which is higher than that in the second day.

It is noted that the system is capable of recording the temperature data for a relatively large number of sleep episodes (e.g., for 180 days).

In some embodiments, the system may further include an environment monitoring device (not depicted in the drawings) communicating with the data processing device 2. The environment monitoring device may be monitoring room temperature, and to provide data regarding the room temperature to the data processing device 2 for further analysis.

In brief, the system as described in the above embodiments has the following advantages.

Firstly, the measuring device 1 of the system is capable of measuring the body temperature during the sleep episode, and to transmit the temperature data to the data processing device 2 for analysis. All processes regarding the calculations may be implemented using the processing unit 23 of the data processing device 2 without human input. As such, potential subjective factors and reliability issues associated with human input may be eliminated. Moreover, the measuring device 1 is embodied using a thermometer patch and the data processing device 2 is embodied using a portable electronic device, such that that the entire system is portable and is relatively convenient to carry compared to an EEG device.

Figure 6:
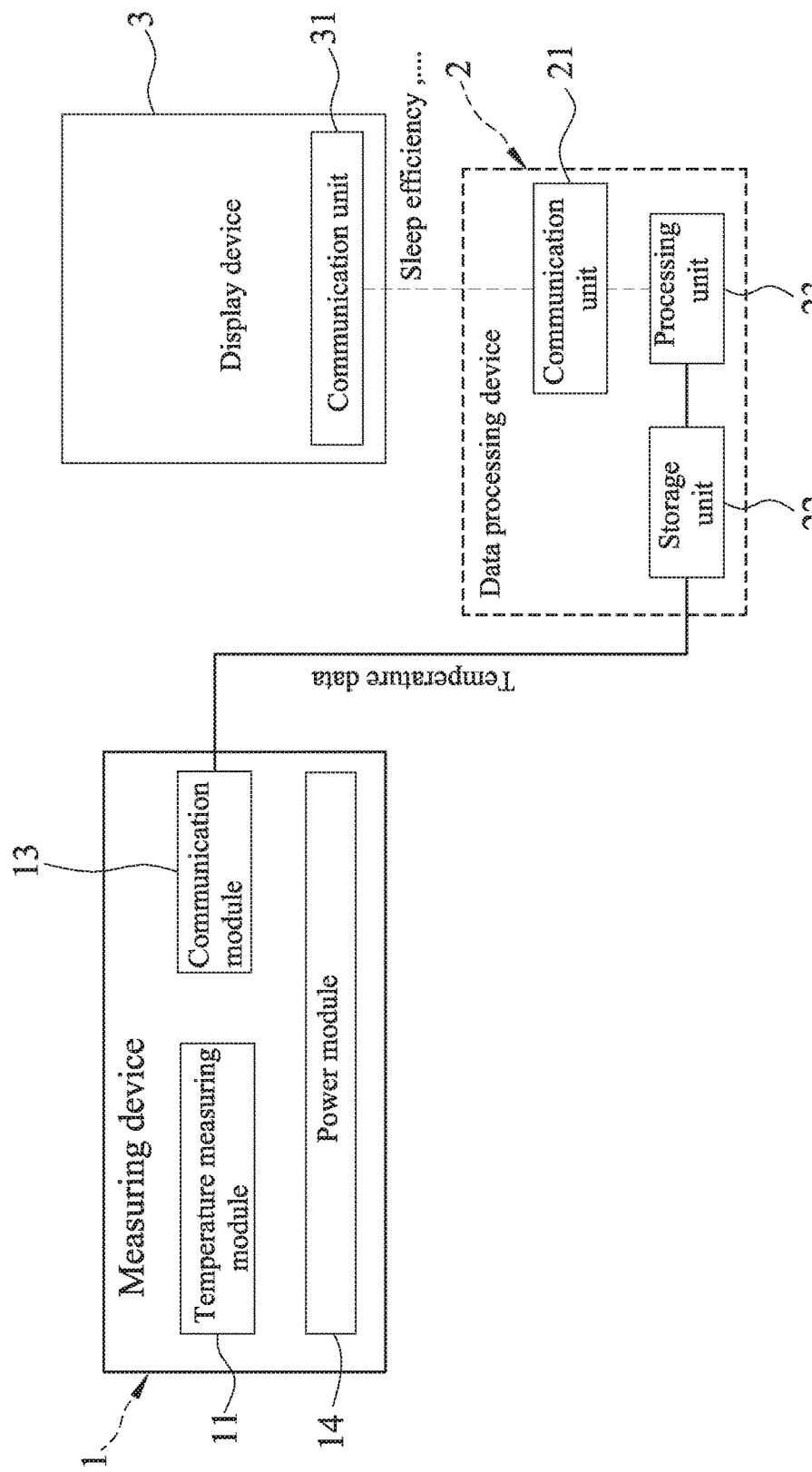
FIG. 6 is a block diagram illustrating a system for monitoring sleep efficiency, according to one embodiment of the disclosure.

FIG. 6 is a block diagram illustrating a system for monitoring sleep efficiency, according to one embodiment of the disclosure.

In this embodiment, the measuring device 1 may be embodied using a thermometer patch as described in the embodiment in FIG. 1 or an infrared temperature measuring component, but the storage module 12 is omitted, and the temperature data is directly transmitted to the data processing device 2 for processing. This way, the measuring device 1 may be manufactured with a smaller size.

To sum up, the embodiments of the disclosure provide a system for sleep monitoring that incorporates the advantages as described above and is implemented with a lower cost and size.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A system for monitoring sleep efficiency, comprising:
a measuring device for measuring body temperature of a subject and for outputting temperature data associated with the body temperature; and
a data processing device coupled with said measuring device for receiving the temperature data therefrom, and programmed to process the temperature data so as to determine sleep efficiency;
wherein the processing of the temperature data includes constructing a curve of the body temperature over a sleep episode, finding a saddle point of the curve occurring for a first time, treating a time instance at which the saddle point occurs as a sleep-onset time point at which the subject falls asleep, and determining the sleep efficiency according to the sleep-onset time point;
wherein said data processing device is programmed to process the temperature data to further define an into-bed time point as a time instance at which said measuring device is activated to measure the body temperature of the subject, and said data processing device determines the sleep efficiency based on the into-bed time point and the sleep-onset time point;
wherein said processing device is further programmed to:
obtain an initial degree of the body temperature at the into-bed time point;
determine an awakening time point at which the subject awakens from sleep as a time instance when the body temperature rises and stays above the initial degree until the end of the sleep episode; and
calculate a total sleep time based on the into-bed time point and the awakening time point.

2. The system of claim 1, wherein said data processing device is programmed to process the temperature data to further obtain at least one of:
an into-bed time point at which the subject goes to bed;
an initial degree of the body temperature at the into-bed time;
a sleep latency from the into-bed time point to the sleep-onset time point;
an awakening time point at which the subject awakens from sleep;
a total sleep time between the into-bed time point and the awakening time point;
a sleep status report indicating a number of changes between light sleep and deep sleep during the sleep episode; and
a sleep quality degree based on the sleep status report.

3. The system of claim 1, wherein said data processing device is further programmed to calculate a sleep latency from the into-bed time point to the sleep-onset time point, and said processing device is programmed to determine that the sleep efficiency as poor when the sleep latency is not shorter than a predetermined threshold.

4. The system of claim 1, wherein:
said measuring device includes
a temperature measuring module that measures the body temperature of the subject and generates the temperature data,
a storage module that stores the temperature data therein,
a communication module that outputs the temperature data stored in said storage module, and
a power module for powering said measuring device;
said processing device includes
a communication unit for communicating with said communication module so as to receive the temperature data,
a storage unit that stores the temperature data received by said communication unit, and
a processing unit that is programmed to process the temperature data and to determine the sleep efficiency.

5. The system of claim 1, wherein:
said measuring device includes a temperature measuring module that measures the body temperature of the subject and generates the temperature data;
said processing device is electrically connected to said temperature measuring module for receiving the temperature data, and includes
a storage unit that stores the temperature data received from said measuring module, and
a processing unit that is programmed to process the temperature data and to determine the sleep efficiency.

6. The system of claim 1, further comprising:
a display device that communicates with said processing device, that receives data related to the sleep efficiency and outputted by said processing device, and that is programmed to display the sleep efficiency according to the data.

* * * * *